US010765632B2

(12) United States Patent
Germain et al.

(10) Patent No.: US 10,765,632 B2
(45) Date of Patent: *Sep. 8, 2020

(54) METHODS OF IMPROVING DELIVERY OF COMPOUNDS FOR THERAPY, PROPHYLAXIS OR DIAGNOSIS (71) Applicant: CURADIGM SAS, Paris (FR)

(72) Inventors: Matthieu Germain, Champigny sur Marne (FR); Marie-Edith Meyre, Saint Mande (FR); Agnes Pottier, Paris (FR); Laurent Levy, Paris (FR)

(73) Assignee: CURADIGM SAS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/529,106

(22) PCT Filed: Nov. 24, 2015

(86) PCT No.: PCT/EP2015/077425
§ 371 (c)(1),
(2) Date: May 24, 2017

(87) PCT Pub. No.: WO2016/083333
PCT Pub. Date: Jun. 2, 2016

(65) Prior Publication Data
US 2017/0258721 A1  Sep. 14, 2017

(30) Foreign Application Priority Data
Nov. 25, 2014 (EP) .................... 14306875

(51) Int. Cl.
*A61K 9/127* (2006.01)
*A61K 47/69* (2017.01)
*A61K 9/00* (2006.01)
*A61P 35/00* (2006.01)
*A61K 9/51* (2006.01)
*A61K 31/704* (2006.01)

(52) U.S. Cl.
CPC ............ *A61K 9/1271* (2013.01); *A61K 9/127* (2013.01); *A61K 9/51* (2013.01); *A61K 31/704* (2013.01); *A61K 47/6911* (2017.08); *A61K 9/0009* (2013.01); *A61K 9/0019* (2013.01)

(58) Field of Classification Search
None
See application file for complete search history.

(56) References Cited

U.S. PATENT DOCUMENTS

| 4,280,918 | A | 7/1981 | Homola et al. |
| 8,845,507 | B2 | 9/2014 | Levy et al. |
| 10,391,058 | B2* | 8/2019 | Germain ............... A61K 9/127 |
| 10,413,509 | B2* | 9/2019 | Pottier ................. A61K 9/0014 |
| 2005/0090732 | A1 | 4/2005 | Ivkov et al. |
| 2006/0264804 | A1* | 11/2006 | Karmon ............... A61N 1/0412 604/20 |
| 2007/0088414 | A1* | 4/2007 | Campbell ............. A61K 9/0019 607/101 |
| 2008/0187595 | A1 | 8/2008 | Jordan et al. |
| 2008/0193372 | A1* | 8/2008 | Lanza .................. A61K 9/1075 424/1.11 |
| 2009/0092661 | A1* | 4/2009 | Huang ................. A61K 9/1271 424/450 |
| 2011/0027375 | A1 | 2/2011 | Tillement et al. |
| 2011/0213192 | A1 | 9/2011 | Levy et al. |
| 2014/0056813 | A1 | 2/2014 | Pottier et al. |
| 2014/0186447 | A1 | 7/2014 | Desai |
| 2014/0271489 | A1 | 9/2014 | Grinstaff et al. |
| 2016/0184225 | A1* | 6/2016 | Pottier ................. A61K 31/704 424/490 |
| 2016/0310614 | A1 | 10/2016 | Pottier et al. |
| 2017/0258717 | A1 | 9/2017 | Germain et al. |
| 2017/0258718 | A1 | 9/2017 | Meyre et al. |

(Continued)

FOREIGN PATENT DOCUMENTS

EP  2 000 150  12/2008
EP  2 537 530  12/2012

(Continued)

OTHER PUBLICATIONS

Thongborisute et al., Pharmazie, 61, pp. 106-111. (Year: 2006).*
He, C. et al. "Effects of particle size and surface charge on cellular uptake and biodistribution of polymeric nanoparticles" *Biomaterials*, May 1, 2010, pp. 3657-3666, vol. 31, No. 13.
"NCL Method PCC-2 Measuring Zeta Potential of Nanoparticles" Nov. 1, 2009, Retrieved from the Internet: URL:http://ncl.cancer.gov/NCL_Method_PCC-2.pdf on Feb. 23, 2015, pp. 1-14.
Written Opinion in International Application No. PCT/EP2015/077425, dated Jan. 15, 2016, pp. 1-6.

(Continued)

*Primary Examiner* — Abigail Vanhorn
(74) *Attorney, Agent, or Firm* — Saliwanchik, Lloyd & Eisenschenk (57) ABSTRACT

The present invention relates to a pharmaceutical composition comprising the combination of (i) at least one biocompatible nanoparticle and (ii) at least one carrier comprising at least one pharmaceutical compound, to be administered to a subject in need of such a pharmaceutical compound, wherein the combination of the at least one biocompatible nanoparticle and of the at least one carrier comprising the pharmaceutical compound(s) potentiates the compound(s) of interest effectiveness in therapy, prophylaxis or diagnosis. The invention also relates to such a composition for use for administering the pharmaceutical compound(s) in a subject in need thereof, wherein the at least one biocompatible nanoparticle and the at least one carrier comprising the at least one pharmaceutical compound are to be administered separately in a subject in need of said pharmaceutical compound, typically between more than 5 minutes and about 72 hours one from each other.

16 Claims, 3 Drawing Sheets

(56) References Cited

U.S. PATENT DOCUMENTS

| | | |
|---|---|---|
| 2017/0258720 A1 | 9/2017 | Pottier et al. |
| 2017/0258937 A1 | 9/2017 | Meyre et al. |

FOREIGN PATENT DOCUMENTS

| | | |
|---|---|---|
| FR | 2 922 106 | 4/2009 |
| JP | H10-120597 | 5/1998 |
| WO | WO 96/35415 | 11/1996 |
| WO | WO 2005/063305 | 7/2005 |
| WO | WO 2005/086639 | 9/2005 |
| WO | WO 2007/116954 | 10/2007 |
| WO | WO 2007/128066 | 11/2007 |
| WO | WO 2009/081287 | 7/2009 |
| WO | WO 2009/105774 | 8/2009 |
| WO | WO 2009/142754 | 11/2009 |
| WO | WO 2009/147214 | 12/2009 |
| WO | WO 2010/048623 | 4/2010 |
| WO | WO 2011/070324 | 6/2011 |
| WO | WO 2011/119988 | 9/2011 |
| WO | WO 2011/151631 | 12/2011 |
| WO | WO 2012/051220 | 4/2012 |
| WO | WO 2012/104275 | 8/2012 |
| WO | WO 2012/104277 | 8/2012 |
| WO | WO 2014/039874 | 3/2014 |
| WO | WO 2014/057432 | 4/2014 |
| WO | WO 2014/191569 | 12/2014 |
| WO | WO 2015/091888 | 6/2015 |

OTHER PUBLICATIONS deKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.

Maggiorella, L. et al. "Nanoscale radiotherapy with hafnium oxide nanoparticles" *Future Oncology*, Sep. 1, 2012, pp. 1167-1181, vol. 8, No. 9.

Written Opinion in International Application No. PCT/EP2014/078619, dated Mar. 26, 2015, pp. 1-6.

Bhatt, N. et al. "Stability study of O/W emulsions using zeta potential" *Journal of Chemical and Pharmaceutical Research*, 2010, pp. 512-527, vol. 2, No. 1.

Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.

Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.

Written Opinion in International Application No. PCT/EP2015/077423, dated Jan. 21, 2016, pp. 1-5.

Belisario, M. A. et al. "Effect of avarol, avarone and nine of their natural and synthetic derivatives on microsomal drug-metabolizing enzymes" *Toxicology Letters*, 1991, pp. 183-193, vol. 57.

Michalets, E. L. et al. "Update: Clinically Significant Cytochrome P-450 Drug Interactions" *Pharmacotherapy*, 1998, pp. 84-112, vol. 18, No. 1.

Written Opinion in International Application No. PCT/EP2015/077441, dated Feb. 3, 2016, pp. 1-6.

Written Opinion in International Application No. PCT/EP2015/077446, dated Feb. 3, 2016, pp. 1-6.

Banquy, X. et al. "Effect of mechanical properties of hydrogel nanoparticles on macrophage cell uptake" *Soft Matter*, Jan. 1, 2009, pp. 3984-3991, vol. 5, No. 20.

Written Opinion in International Application No. PCT/EP2015/077438, dated Jan. 27, 2016, pp. 1-7.

Abra, RM. et al. "Liposome Disposition in Vivo: Effects of Pre-Dosing with Liposomes" *Research Communications in Chemical Pathology and Pharmacology*, Aug. 1980, pp. 349-360, vol. 29, No. 2.

Ogu, C. C. et al. "Drug interactions due to cytochrome P450" *BUMC Proceedings*, Oct. 2000, pp. 421-423, vol. 13.

Abu Lila, A. S. et al. "Oxaliplatin encapsulated in PEG-coated cationic liposomes induces significant tumor growth suppression via a dual-targeting approach in a murine solid tumor model" *Journal of Controlled Release*, 2009, pp. 8-14, vol. 137.

Gabizon, A. A. "Liposome circulation time and tumor targeting: implications for cancer chemotherapy" *Advanced Drug Delivery Reviews*, 1995, pp. 285-294, vol. 16.

Harashima, H. et al. "Size Dependent Liposome Degradation in Blood: In Vivo/In Vitro Correlation by Kinetic Modeling" *Journal of Drug Targeting*, 1995, pp. 253-261, vol. 3.

Hadaruga, D. I. et al. "Liposomes containing titanium dioxide nanoparticles (Short communication)" *Journal of Agroalimentary Processes and Technologies*, 2010, pp. 62-66, vol. 16, No. 1.

Shamsipour, F. et al. "Conjugation of Monoclonal Antibodies to Super Paramagnetic Iron Oxide Nanoparticles for Detection of her2/neu Antigen on Breast Cancer Cell Lines" *Journal of Medical Biotechnology*, Apr.-Jun. 2009, pp. 27-31, vol. 1, No. 1.

Kim, J.-Y. et al. "In-vivo tumor targeting of pluronic-based nano-carriers" *Journal of Controlled Release*, 2010, pp. 109-117, vol. 147.

Yu, M. K. et al. "Drug-Loaded Superparamagnetic Iron Oxide Nanoparticles for Combined Cancer Imaging and Therapy in Vivo" *Angew. Chem. Int. Ed.*, 2008, pp. 5362-5365, vol. 47.

Choi, W. I. et al. "The effect of mechanical properties of iron oxide nanoparticle-loaded functional nano-carrier on tumor targeting and imaging" *Journal of Controlled Release*, 2012, pp. 267-275, vol. 162.

Liang, X. et al. "Mechanical properties and stability measurement of cholesterol-containing liposome on mica by atomic force microscopy" *Journal of Colloid and Interface Science*, 2004, pp. 53-62, vol. 278.

Nie, Y. et al. "Cholesterol Derivatives Based Charged Liposomes for Doxorubicin Delivery: Preparation, In Vitro and In Vivo Characterization" *Theranostics*, 2012, pp. 1092-1103, vol. 2, No. 11.

Yu, S. et al. "Carboxyl group ($-CO_2H$) functionalized ferrimagnetic iron oxide nanoparticles for potential bio-applications" *Journal of Materials Chemistry*, 2004, pp. 2781-2786, vol. 14.

Ismail, M.F. et al. "Potential therapeutic effect of nanobased formulation of rivastigmine on rat model of Alzheimer's disease" *International Journal of Nanomedicine*, 2013, pp. 393-406, vol. 8.

Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.

Written Opinion in International Application No. PCT/EP2014/061296, dated Sep. 5, 2014, pp. 1-9.

Olson, F. et al. "Preparation of Liposomes of Defined Size Distribution by Extrusion Through Polycarbonate Membranes" *Biochimica et Biophysica Acta*, 1979, pp. 9-23, vol. 557.

Lu, H. et al. "Drug-target residence time: critical information for lead optimization" *Current Opinion in Chemical Biology*, 2010, pp. 467-474, vol. 14.

Copeland, R. A. et al. "Drug-target residence time and its implications for lead optimization" *Nature Reviews/Drug Discovery*, Sep. 2006, pp. 730-739, Corrigendum (1 page), vol. 5.

Simoes, S. et al. "Cationic liposomes for gene delivery" *Expert Opinion in Drug Delivery*, 2005, pp. 237-254, vol. 2, No. 2.

Singh, R. et al. "Nanoparticle-based targeted drug delivery" *Experimental and Molecular Pathology*, 2009, pp. 215-223, vol. 86.

Lai, B.-H. et al. "Surface modification of iron oxide nanoparticles with polyarginine as a highly positively charged magnetic nano-adsorbent for fast and effective recovery of acid proteins" *Process Biochemistry*, 2012, pp. 799-805, vol. 47.

\* cited by examiner

FIGURE 1

Compound of interest

Carrier lacking of sterically stabilizing agent

Sterically stabilizing agent

Biocompatible nanoparticles having a longest dimension between about 4 nm and about 500 nm and an absolute surface charge value of at least |10 mV|

METHODS OF IMPROVING DELIVERY OF COMPOUNDS FOR THERAPY, PROPHYLAXIS OR DIAGNOSIS

CROSS-REFERENCE TO RELATED APPLICATION

This application is the U.S. national stage application of International Patent Application No. PCT/EP2015/077425, filed Nov. 24, 2015.

FIELD OF THE INVENTION

The invention relates to a pharmaceutical composition comprising the combination of (i) at least one biocompatible nanoparticle and (ii) at least one carrier comprising at least one compound of interest, typically at least one pharmaceutical compound, to be administered to a subject in need of such at least one compound of interest, wherein the combination of the at least one biocompatible nanoparticle and of the at least one carrier comprising at least one compound of interest potentiates the compound(s) of interest's efficiency. The longest dimension of the biocompatible nanoparticle is typically between about 4 and about 500 nm, and its absolute surface charge value is of at least 10 mV (|10 mV|). The carrier is devoid of any surface sterically stabilizing agent.

The invention also relates to such a composition for use for administering the compound(s) of interest in a subject in need thereof, wherein the at least one nanoparticle on one side and the at least one carrier comprising the compound(s) of interest on the other side are preferably to be administered in said subject sequentially, typically between more than 5 minutes and about 72 hours one from each other.

The combined, and typically sequential, administration to the subject of the at least one biocompatible nanoparticle and of the at least one carrier comprising the compound(s) of interest maintains the pharmaceutical (i.e. therapeutic, prophylactic or diagnostic) benefit of said compound(s) of interest for a reduced toxicity thereof in said subject, or increases its pharmaceutical benefit for an equivalent or reduced toxicity, when compared to the pharmaceutical benefit and toxicity induced by said compound(s) when administered at the standard pharmaceutical dose, typically in the absence of any biocompatible nanoparticle and/or carrier.

The pharmaceutical composition of the invention typically allows a reduction of at least 10% of the administered compound(s) pharmaceutical dose(s) when compared to the standard pharmaceutical dose(s) of said compound(s), typically in the absence of any biocompatible nanoparticle and/or carrier, while maintaining the same pharmaceutical benefit for an equivalent toxicity, preferably a reduced toxicity, for the subject, or while increasing the pharmaceutical benefit for an equivalent or reduced toxicity for the subject.

BACKGROUND

The use of nanotechnologies to deliver therapeutic and diagnostic agents in a safer and more efficient manner to patients has led to an increased interest in the field during the last decades. Drug delivery systems, typically carriers such as liposomes, emulsions or micelles, intended to maximize the therapeutic efficacy of drugs thanks to the control of their biodistribution profile have emerged. Those systems offer the possibility to encapsulate a poorly soluble drug, to protect a drug from destruction or elimination, and/or to modify the blood circulation and distribution of a drug.

The observed rapid blood clearance of the first generation of drug delivery systems (DDSs) (due to their capture by the mononuclear phagocytic system (MPS)) has prompted the development of a second generation of DDSs exhibiting a surface modified by sterically stabilizing agents selected to bring "stealth" properties to the DDS when attached to its surface. These agents are typically flexible and/or hydrophilic polymers, such as polyethylene glycol (PEG) polymers and typically may bring surface charges that are slightly negative or positive. Steric stabilization prevents non-specific binding of the DDS's surface to blood components and reduce its rapid uptake and clearance in vivo by cells of the mononuclear phagocytic system (MPS), leading to prolonged DDS blood circulation times [Jain K. R. and Stylianopoulos T. Delivering nanomedicine to solid tumors. Nature Reviews. Clinical Oncology 2010, 7, 653-664]. Liposomal long-circulating nanoparticulate pharmaceutical drug delivery systems (NDDSs) are the most frequently studied type of NDDS; however, synthetic amphiphilic polymers have also been used to sterically stabilize other types of NDDS to alter their biodistribution [Torchilin V. P. Multifunctional, stimuli-sensitive nanoparticulate systems for drug delivery. Nature Reviews. Drug Discovery 2014, 13, 813-827].

Despite of this increased blood circulation time (i.e. enhanced blood transportation), which was thought as beneficial for the delivery of the therapeutic compound to its target site, the flexible and/or hydrophilic polymer coating, typically the PEG coating, was found to compromise the intracellular delivery of the pharmaceutical compound (i.e. the release of the compound at its target site), which ultimately resulted in a loss of activity for the delivery system. A way to overcome this limitation is to use cleavable PEG systems. However, the increase complexity in the design of such carriers may generate difficulties in the reproducibility of the carrier surface properties, resulting in batch-to batch unacceptable variability. Moreover, the extent of exposure of those "stealth" DDS has been related with more adverse events. DOXIL, a PEGylated liposomal formulation comprising doxorubicin, was for instance found to produce serious adverse events, such as the hand-foot syndrome or mucositis. The hydrophilic coating of the liposomes was questioned as perhaps facilitating their accumulation in ecerine sweat gland in palms and planta [Pegylated liposomal doxorubicin-related palmar-plantar erythrodysesthesia ('hand-foot' syndrome). D. Lorusso et al. Annals of Oncology. 2007; 18, 1159-1164].

WO2005/063305 relates to an assembly comprising a gas-filled microvesicle (with a size typically of at least 0.5 μm) and a component (with a size about below 100 nm) associated to said microvesicle. The resulting assembly is to be used as a pharmaceutically active component in diagnostically and/or therapeutically active formulations. The two components, i.e. the gas-filled microvesicle and the microvesicle associated component, are administered simultaneously typically for enhancing the imaging in the field of ultrasound contrast imaging, including targeted ultrasound imaging, ultrasound-mediated drug delivery and other imaging techniques.

As apparent from the prior art and despite of a long medical need, the safe and efficient delivery of pharmaceutical compounds (including therapeutic, prophylactic as well as diagnostic compounds) to their target site(s) remains a concern. There is a clear need to improve the compound's efficacy and safety, or in other words the pharmaceutic compound's transport and release, in order for said compound to reach its target site in a subject in the necessary and sufficient quantity to get the desired diagnostic, therapeutic or prophylactic effect.

DETAILED DESCRIPTION

The present invention now allows optimization of the efficiency of a compound of interest (herein also simply identified as "the compound") whatever its intended use in the context of therapy, prophylaxis or diagnostic. The composition herein described which is a combination of (i) at least one biocompatible nanoparticle and of (ii) at least one carrier comprising at least one compound of interest, optimize the at least one compound of interest's pharmacokinetic parameters, and, as a consequence, now renders possible the development of pharmaceutic compounds which could not have been developed otherwise due for example to their unacceptable toxicity. Typically, the biocompatible nanoparticle is not used as such as a pharmaceutical compound, i.e. as a therapeutic, prophylactic or diagnostic compound.

A typical composition of the invention (herein generally identified as "pharmaceutical composition") is a composition comprising the combination of (i) at least a biocompatible nanoparticle and (ii) at least a carrier comprising at least one compound ("the compound of interest"), wherein the longest or largest dimension of the biocompatible nanoparticle is typically between about 4 nm and about 500 nm, and the absolute surface charge value of the biocompatible nanoparticle is of at least 10 mV, and wherein the carrier is devoid of any surface sterically stabilizing agent, i.e. devoid of flexible and/or hydrophilic polymer, preferably devoid of hydrophilic polymer bearing a slightly negative or positive charge to the carrier's surface, such as PEG.

Typically, the ratio between the (at least one) biocompatible nanoparticles and the (at least one) carriers comprising at least one compound of interest is between 0.1/1 and 1000/1 or 0.5/1 and 1000/1, preferably between 0.5/1 and 500/1, even more preferably between 0.5/1 and 300/1.

The terms "about" and "around" when associated to a value such as for example a nanoparticle' size or a time interval indicates that a variation with the indicated value, which would be recognized by the skilled person as small variation, does not substantially impact the properties of the subject-matter it is associated to and that said subject-matter remains in the spirit of the claimed invention.

A preferred objet of a the invention is a pharmaceutical composition comprising the combination of (i) at least one biocompatible nanoparticle and of (ii) at least one carrier comprising at least one compound of interest, typically at least one pharmaceutical compound, wherein the longest or largest dimension of the biocompatible nanoparticle is between about 4 nm and about 500 nm, and the absolute surface charge value of the biocompatible nanoparticle is of at least 10 mV (|10 mV|), and wherein the carrier is devoid of any surface sterically stabilizing agent, for use for administering the at least one compound of interest in a subject in need thereof, wherein the at least one biocompatible nanoparticle on one side and the at least one carrier comprising the at least one compound of interest on the other side are preferably to be administered separately in a subject in need of said at least one compound of interest, typically between more than 5 minutes and about 72 hours one from each other, and wherein the biocompatible nanoparticle is not used as such as a pharmaceutical compound.

The combined, and typically sequential, administration to the subject of the at least one biocompatible nanoparticle and of the at least one carrier comprising the compound(s) of interest, through the composition of the invention, typically allows (maintains) the same pharmaceutical (i.e. therapeutic, prophylactic or diagnostic) benefit of the compound(s) for a reduced toxicity thereof for the subject, or increase the pharmaceutical benefit of the compound(s) for an equivalent or reduced toxicity thereof for the subject (preferably a reduced toxicity), when compared to pharmaceutical benefit and toxicity induced by the standard pharmaceutical dose of said compound(s), typically in the absence of any biocompatible nanoparticle and/or carrier.

The pharmaceutical composition of the invention typically allows a reduction of at least 10%, preferably at least 15%, of the administered pharmaceutical (i.e. therapeutic, prophylactic or diagnostic) compound(s) dose(s) when compared to the standard pharmaceutical dose(s) of said compound(s), typically in the absence of any biocompatible nanoparticle and/or carrier, (i) while maintaining the same pharmaceutical benefit for an equivalent toxicity, preferably a reduced toxicity, for the subject or (ii) while increasing the pharmaceutical benefit for an equivalent or reduced toxicity for the subject.

The Biocompatible Nanoparticle

As the shape of the particle can influence its "biocompatibility", particles having a quite homogeneous shape are herein preferred. For pharmacokinetic reasons, nanoparticles being essentially spherical/round or ovoid in shape are thus preferred. Such a shape also favors the nanoparticle interaction with or uptake by cells. Spherical/round shape is particularly preferred.

In the spirit of the invention, the term "nanoparticle" refers to a product, in particular a synthetic product, with a size in the nanometer range, typically between about 1 nm and about 500 nm, preferably between about 4 nm and about 500 nm, between about 4 and about 400 nm, about 30 nm and about 300 nm, about 20 nm and about 300 nm, about 10 nm and about 300 nm, for example between about 4 nm and about 100 nm, for example between about 10 nm, 15 nm or 20 nm and about 100 nm, or between about 100 nm and about 500 nm, typically between about 100 nm and about 300 nm.

The terms "size of the nanoparticle", "largest size of the nanoparticle" and "longest size of the nanoparticle" herein typically refer to the "longest or largest dimension of the nanoparticle" or "diameter of the nanoparticle" when spherical/round or ovoid in shape. Transmission Electron Microscopy (TEM) or Cryo-TEM can be used to measure the size of the nanoparticle. As well, Dynamic Light Scattering (DLS) can be used to measure the hydrodynamic diameter of nanoparticles in solution. These two methods may further be used one after each other to compare the hydrodynamic diameter of a nanoparticle measured by DLS with the size of said nanoparticle measured by TEM or Cryo-TEM, in order to confirm said size. A preferred method is DLS (Ref. International Standard ISO22412 Particle Size Analysis—Dynamic Light Scattering, International Organisation for Standardisation (ISO) 2008).

To be usable in the context of the invention, the absolute electrostatic surface charge (also herein identified as "charge" or "surface charge") of the biocompatible nanoparticle is to be higher than |10 mV| (absolute value). The surface charge of a nanoparticle is typically determined by zeta potential measurements in aqueous medium for a nanoparticles concentration between 0.2 and 10 g/L, for a pH between 6 and 8, and typically for electrolytes concentrations in the aqueous medium between 0.001 and 0.2 M, for example 0.01 M or 0.15 M.

Typically, the biocompatible nanoparticle of the present invention has an electronic surface charge of at least |10 mV|, i.e. below −10 mV or above +10 mV, for example below between −12 mV or −15 mV and −20 mV or above between +12 mV or +15 mV and +20 mV, typically below −15 mV or above +15 mV. Preferably, the biocompatible nanoparticle of the present invention has an absolute electronic surface charge value ("absolute surface charge value") of more than 10 mV, said charge being even more preferably a negative charge.

The combined properties, size and surface charge of the nanoparticles, allow for a short blood circulation of the nanoparticles and extravasation into the liver organ. Therefore, by sequentially administering the biocompatible nanoparticles of the invention and the carrier comprising the compound(s) of interest, no co-circulation or a limited co-circulation of the two compounds (i.e. of the biocompatible nanoparticle and of carrier comprising the compound(s) of interest), is achieved. Therefore, the combined properties of the biocompatible nanoparticles, size and surface charge, permit the safe use of the compound(s) of interest while allowing (maintaining) the same pharmaceutical (i.e. therapeutic, prophylactic or diagnostic) benefit of the compound(s) for a reduced toxicity thereof for the subject, or in other words while increasing the pharmaceutical benefit of the compound(s) for an equivalent or reduced toxicity thereof for the subject (preferably a reduced toxicity), when compared to pharmaceutical benefit and toxicity induced by the standard pharmaceutical dose of said compound(s), typically in the absence of any biocompatible nanoparticle and/or carrier.

So long as it is charged, the nanoparticle usable in the context of the invention can be either organic or inorganic. A mixture of organic and inorganic nanoparticles can further be used.

When organic, the nanoparticle can be a lipid-based nanoparticle (glycerolipid, phospholipid, sterol lipid, etc.), such as a solid-lipid nanoparticle, a protein-based nanoparticle also herein identified as "protein-nanoparticle" (albumin for instance), a polymer-based nanoparticle ("polymeric nanoparticle"), a co-polymer-based nanoparticle ("co-polymeric nanoparticle"), a carbon-based nanoparticle, a virus-like nanoparticle (for example a viral vector).

The organic nanoparticle may further be a nanosphere (plain nanoparticle) or a nanocapsule (hollow nanoparticle) such as a liposome, a gel, a hydrogel, a micelle, a dendrimer, etc. A mixture of the herein described organic nanoparticles can also be used. The polymer or co-polymer can be of natural or synthetic origin.

Examples of synthetic (artificial) and natural polymers or co-polymers usable in the context of the invention to prepare organic nanoparticles can be selected from polylactic acid (PLA), Poly (lactide-co-glycolic) acid (PLGA), Polyethyleneglycol (PEG), Polyglactin, Polylactide, Polyoxyethylene fatty acid esters, Polypropylene glycol, Polysorbate, Polyvinyl alcohol, Polyacrylamide, Polymethylmethacrylate, Polyalkylcyanoacrylate, Polylactate-co-glycolate, Poly (amido amine), Poly(ethyleneimine), alginate, cellulose and cellulose derivatives polymers, collagen, hyaluronic acid, polyglutamic acid (PGA), actin, polysaccharide, and gelatin.

When inorganic and when its longest dimension is typically below about 10 nm, for example below about 8 nm, below about 7 nm, typically comprised between about 7 nm and about 4 nm, for example below about 6 nm, below about 5 nm or below about 4 nm, the nanoparticle may be made of any inorganic material. The inorganic material may for example comprise metallic element from period 3, 4, 5, 6 of the Mendeleev's periodic table, including the lanthanides. When the longest dimension of the nanoparticle is typically below about 10 nm, the nanoparticles may assemble in larger structures. Assembling of nanoparticles in larger structure may typically be triggered by interactions between nanoparticles and a biocompatible polymer(s), protein(s), etc. Larger structure may also be obtained by trapping the nanoparticles in a carrier, typically a plain carrier such as gelatin structure (also herein identified as "gelatin nanoparticle") or a hollow carrier such as liposome. After in vivo administration, those larger structures can further be designed by the skilled person to release the nanoparticles.

When inorganic and when the longest dimension of said nanoparticle is typically of at least 10 nm, typically between 10 and 500 nm, the nanoparticle may comprise at least one of, or may consist in (i) one or more divalent metallic elements selected for example from Mg, Ca, Ba and Sr, (ii) one or more trivalent metallic element selected for example from Fe and Al, and (iii) one or more tetravalent metallic element comprising Si.

In a particular embodiment, the inorganic material of the nanoparticle is selected from (i) one or more divalent metallic elements selected for example from Mg, Ca, Ba and Sr (ii) one or more trivalent metallic element selected for example from Fe and Al and (iii) one or more tetravalent metallic element comprising Si.

In a further particular embodiment, the inorganic material of the nanoparticle is selected from calcium carbonate ($CaCO_3$), magnesium carbonate ($MgCO_3$), magnesium hydroxide ($Mg(OH)_2$), iron hydroxide ($Fe(OH)_2$), iron oxyhydroxide (FeOOH), iron oxide ($Fe_3O_4$ or $Fe_2O_3$), aluminium oxide ($Al_3O_4$), aluminium hydroxide ($Al(OH)_3$), aluminium oxyhydroxide (AlOOH) and silicium oxide ($SiO_2$).

The nanoparticles used in the herein described compositions are to be biocompatible, i.e. compatible with living tissues. When required by their composition, the nanoparticles are thus to be coated with a biocompatible material to become usable. In a particular embodiment of the invention, the herein mentioned nanoparticle is thus covered with a biocompatible coating.

The biocompatible material can be an agent allowing interaction with a biological target. Such an agent will typically bring a positive or a negative charge on the nanoparticle's surface when the absolute charge of the nanoparticle is of at least 10 mV.

An agent forming a positive charge on the nanoparticle's surface can be for example selected from aminopropyltriethoxisilane or polylysine. An agent forming a negative charge on the nanoparticle surface can be for example selected from a phosphate (for example a polyphosphate, a metaphosphate, a pyrophosphate, etc.), a carboxylate (for example citrate or dicarboxylic acid, in particular succinic acid) and a sulphate.

In a particular embodiment, as long as the absolute charge of the nanoparticle is of at least 10 mV (|10 mV|), the nanoparticle can be coated with a biocompatible material comprising an agent displaying a steric group, such an agent being also herein identified as a "surface sterically stabilizing agent".

Such an agent displaying a steric group may be selected for example from polyethylene glycol (PEG); polyethylenoxide; polyvinylalcohol; polyacrylate; polyacrylamide (poly(N-isopropylacrylamide)); polycarbamide; a biopolymer, a polysaccharide such as dextran, xylan and cellulose; collagen; a switterionic compound such as polysulfobetain; etc. The biocompatible coating may advantageously be a "full coating" (complete monolayer). This implies the presence of a very high density of biocompatible molecules creating an appropriate charge on the all surface of the nanoparticle. The biocompatible coating may further comprise a labelling agent, typically an agent allowing the visualisation of a color using standard imaging equipment.

The combined administration of the at least one biocompatible nanoparticle together with the at least one carrier comprising the at least one compound of interest maintains the pharmaceutical (i.e. therapeutic, prophylactic or diagnostic), typically therapeutic, benefit of the compound(s) of interest for a reduced toxicity, or increases the pharmaceutical benefit of the compound(s) of interest for an equivalent or reduced toxicity, for the subject, typically when administered in the subject in need of the compound(s) of interest, between more than 5 minutes and about 72 hours one from each other, when compared to pharmaceutical benefit and toxicity induced by the standard pharmaceutical, typically therapeutic, dose(s) of said compound(s), typically in the absence of any biocompatible nanoparticle and/or carrier.

In a particular embodiment, the combined administration of the at least one biocompatible nanoparticle and of the at least one carrier comprising the at least one compound of interest allows a reduction of at least 10%, preferably at least 15%, of the administered compound(s) therapeutic dose, typically when administered in the subject in need of the at least one compound of interest, between more than 5 minutes and about 72 hours one from each other, when compared to the standard therapeutic dose(s) of said compound(s), typically in the absence of any biocompatible nanoparticle and/or carrier, while maintaining the same therapeutic benefit for an equivalent toxicity or a reduced toxicity (preferably a reduced toxicity) of the compound(s) for the subject; or while increasing the therapeutic benefit for an equivalent or reduced toxicity of the compound(s) for the subject. In a particular embodiment, the at least one nanoparticle is administered with several carriers, typically at least two carriers, each of said carrier comprising at least one compound of interest. The compounds of interest present in a first carrier can be identical or different to those present in a second or in another distinct carrier.

The nanoparticle is preferably cleared from the subject to whom it has been administered typically within 1 hour and 6 weeks, for example 1 month (4 weeks), within 1 hour and 1 month, for example between 1 hour and 3 weeks, or between 1 hour and 2 weeks, or between 1 hour and 1 week, following its administration to a subject in need of the compound of interest.

The material constituting the nanoparticle (including its biocompatible coating when present) is important in determining the biopersistence (i.e. the persistence in the subject) of the nanoparticle. The nanoparticle may be regarded as biodegradable (when constituted for example of a biodegradable polymer such as PLGA or PLA) and/or dissolvable (iron oxide for example), or non-biodegradable and non-dissolvable. Biodegradable and dissolvable nanoparticles are more rapidly cleared from the subject than non-biodegradable and/or non-dissolvable nanoparticles.

The Compound of Interest

Different molecules or agents can be used according to the present teaching as the at least one compound of interest, typically as the at least one pharmaceutical compound of interest. This compound may be a therapeutic, a prophylactic or a diagnostic compound as previously explained. It can be an organic compound or an inorganic compound.

Examples of compound usable as the "compound of interest" are typically selected from a small molecule, a cytotoxic compound and a transition metal coordination complex. In the context of the present invention, a small molecule is a low molecular weight (<900 daltons) organic compound with a size of the order of $10^{-9}$ m. Most drugs are small molecules.

In a particular embodiment, the compound of interest used in the context of the present invention is a targeted small molecule. A targeted small molecule generally inhibits enzymatic domains on mutated, overexpressed, or otherwise critical proteins (potential targets in the context of cancer treatment) within the malignant cells. Targeted small molecules include those molecules that target cell division (for example an aurora-kinase inhibitor or a cyclin-dependent-kinase inhibitor), or another biological mechanism such as protein turnover or chromatin modification (for example a histone-deacetylase inhibitor). Examples of targeted small molecules are imatinib, rapamycin, gefitinib, erlotinib, sorafenib, sunitinib, nilotinib, dasatinib, lapatinib, bortezomib, atorvastatin, etc.

In another particular embodiment, the compound of interest used in the context of the present invention is a cytotoxic compound, for example a chemotherapeutic agent. The cytotoxic compound can be for example selected from a DNA-modifying agent, such as an anthracycline (for example doxorubicine, daunorubicine, etc.); an alkylating agent (for example melphalan or temozolomide); and a drug interfering very precisely with defined physiological mechanisms such as microtubule polymerization (for example taxol), or metabolite synthesis (for example methotrexate). In a particular embodiment, the cytotoxic compound is an activable cytotoxic compound. Photofrin is an example of such an activable cytotoxic compound, typically used in the context of Photodynamic Therapy. Photofrin is activated by a laser source to produce its therapeutic effect.

In another particular embodiment, the compound of interest used in the context of the present invention is a transition metal coordination complex. Transition metal coordination complexes offer potential advantages over the more common organic-based drugs, including a wide range of coordination numbers and geometries, accessible redox states, 'tune-ability' of the thermodynamics and kinetics of ligand substitution, as well as a wide structural diversity. Metal-based substances interact with cell molecular targets, affecting biochemical functions resulting in malignant cell destruction. Transition metal coordination complexes are typically cytotoxic agents (for instance, platinum coordination complexes: cisplatin, carboplatin, oxaloplatin, or ruthenium or gold coordination complexes) acting on DNA structures.

The Carrier

Figure 1:
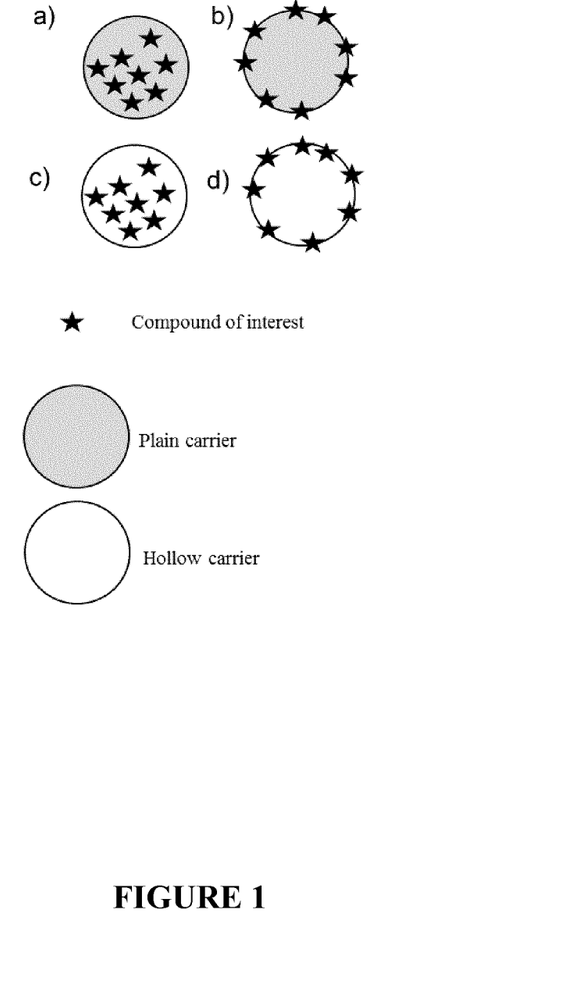
FIG. 1: Schematic representation of carriers devoid of any sterically stabilizing agent comprising at least one compound of interest. The carrier can be a plain carrier (a, b) or a hollow carrier (c, d). The compound of interest is typically entrapped or impregnated (a, c) or grafted (bound) to the carrier with the help of a linker or in the absence of any linker (b, d).

The at least one compound of interest is encapsulated or impregnated in a carrier, or grafted (bound) to such a carrier according to methods known by the skilled person. Schematic representations of carriers comprising at least one compound(s) of interest are presented in FIG. 1.

The carrier can be an organic carrier. The organic carrier is typically selected from a lipidic carrier (for example a glycerolipid, a phospholipid, a sterol, etc.); a polymeric carrier; a co-polymeric carrier; a carbonaceous carrier; and a virus-like carrier (for example a viral vector).

The polymer or co-polymer constituting the carrier can be of natural or synthetic origin. Examples of synthetic (artificial) and natural polymers or co-polymers usable in the context of the invention to prepare the carrier can be selected from polylactic acid (PLA), Poly (lactide-co-glycolic) acid (PLGA), Poly (glutamic acid) (PGA), poly(caprolactone) (PCL), poly (amino acids), Polyglactin, Polylactide, Polyoxyethylene fatty acid esters, Polysorbate, Polyvinyl alcohol, Polyacrylamide, Polymethylmethacrylate, Polyalkylcyanoacrylate, Polylactate-co-glycolate, Poly(amido amine), Poly(ethyleneimine), alginate, cellulose and cellulose derivatives polymers, collagen, hyaluronic acid, actin, polysaccharide, and gelatin.

The carrier can be an inorganic carrier. The inorganic carrier is typically a nanoparticle. The nanoparticle is typically selected from a metal nanoparticle, a metal oxide nanoparticle, and a mixture thereof.

The carrier can be a plain carrier such as a nanosphere (plain nanoparticle) or a hollow carrier such as nanocapsule (hollow nanoparticle).

Preferred carriers are for example selected from a liposome, a micelle, a polymeric (or "polymer") carrier, an hydrogel, a dendrimer, a gel, a co-polymeric carrier, a protein carrier and an inorganic carrier such as herein defined.

The surface of the carrier of the present invention is typically and preferably devoid of (or in other words lacks or does not expose) any surface sterically stabilizing agent, i.e. of any hydrophilic and/or flexible polymer. For instance, the carrier of the present invention is devoid of, or does not expose, a polymer selected from Dextran, polysialic acid (PSA), hyaluronic acid, chitosan, heparin, polyvinyl pyrrolidone (PVP), polyvinyl alcohol (PVA), polyacrylamide, poly (ethylene glycol) (PEG), and a PEG-based copolymer such as poloxamer, poloxamine or polysorbate. Preferably, the carrier of the invention is devoid of any hydrophilic polymer which bring a slightly negative or positive surface charge to the carrier's surface such as poly(ethylene glycol) (PEG) or PEG-based copolymer, polyvinyl alcohol (PVA) or polyvinyl pyrrolidone (PVP).

Figure 2:
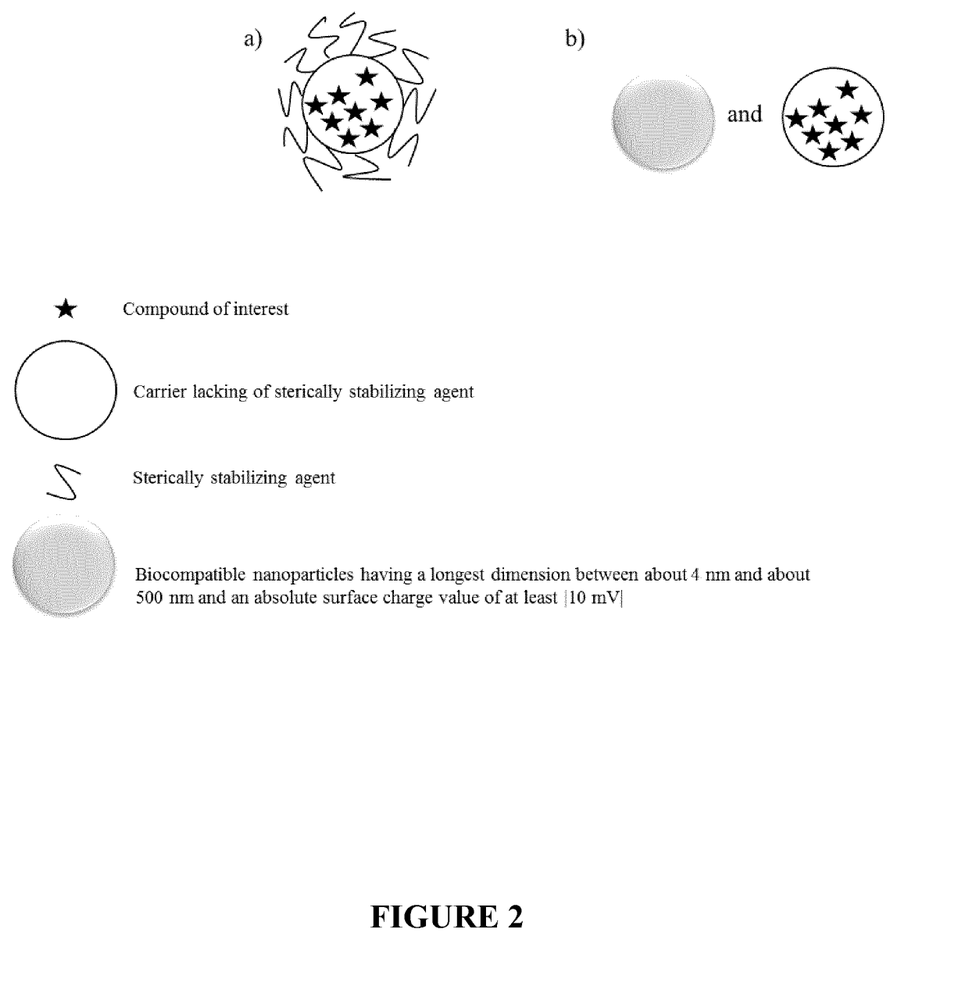
FIG. 2: a) Schematic representation of a carrier comprising at least one compound of interest. The surface of the carrier is modified by a sterically stabilizing agent. b) schematic representation of a pharmaceutical composition according to the invention comprising the combination of (i) at least one biocompatible nanoparticle and of (ii) at least one carrier comprising at least one compound of interest, the carrier being devoid of any sterically stabilizing agent.
Figure 3:
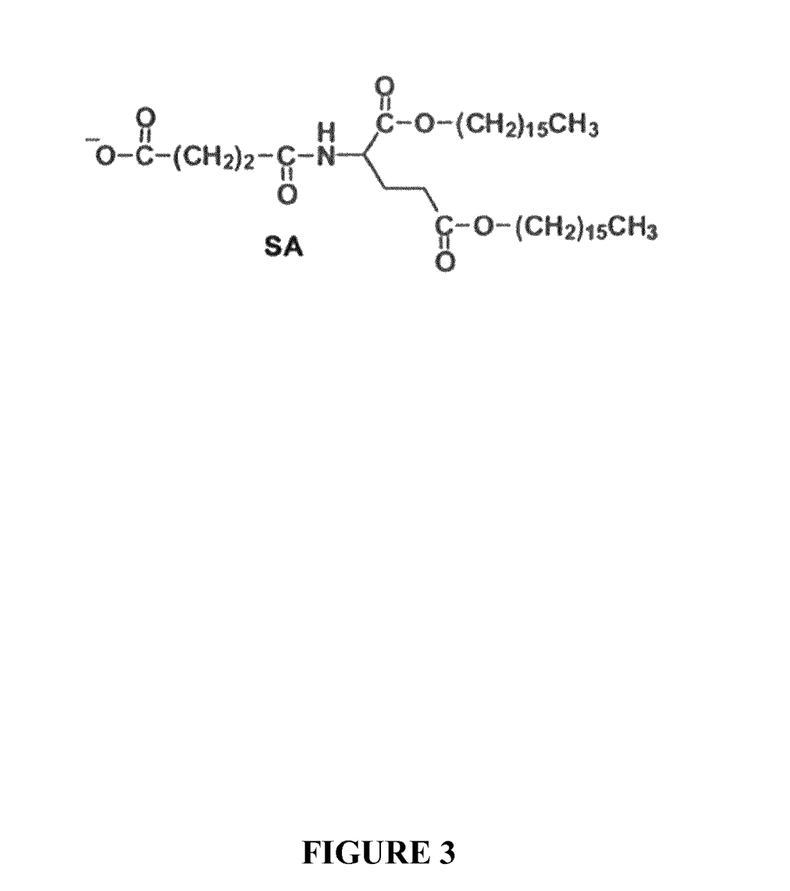
FIG. 3: Chemical formula of L-Glutamic acid, N-(3-carboxy-1-oxopropyl)-, 1,5-dihexaciecyl ester (SA-lipid).

The pharmaceutical composition of the present invention (cf. FIG. 2b) can advantageously be substituted to existing carriers (or drug delivery systems) comprising or exposing a surface sterically stabilizing agent (FIG. 2a) such as typically an hydrophilic and flexible polymer, more particularly an hydrophilic polymer which bring a slightly negative or positive surface charge to the carrier's surface (for example a polyethylene glycol polymer), such a negative or positive surface charged being considered as neutral by the skilled person.

The pharmaceutical composition of the present invention maintains the pharmaceutical (i.e. therapeutic, prophylactic or diagnostic) benefit of the compound of interest for a reduced toxicity thereof in said subject, or increases its pharmaceutical benefit for an equivalent or reduced toxicity, when compared to the pharmaceutical benefit and toxicity induced by said compound when administered at the standard pharmaceutical dose, typically in the absence of any nanoparticle and/or carrier.

The pharmaceutical composition of the invention typically allows a reduction of at least 10% of the administered compound pharmaceutical dose when compared to the standard pharmaceutical dose of said compound, typically in the absence of any nanoparticle and/or carrier, while maintaining the same pharmaceutical benefit for an equivalent toxicity, preferably a reduced toxicity, for the subject, or while increasing the pharmaceutical benefit for an equivalent or reduced toxicity for the subject.

The carrier allows the release of the compound of interest preferably in a controlled manner. The carrier can typically be engineered to release the compound(s) of interest at a predetermined or tunable rate, or in response to an external stimulus.

In a particular embodiment, the carrier allows the release of the compound(s) of interest typically by temporal-controlled release, by diffusion of the compound of interest from the carrier, by erosion and/or by degradation of the carrier.

In another particular embodiment, the carrier allows the release of the compound(s) of interest thanks to an intracellular or extra-cellular activation, i.e. in response to an intracellular or an extracellular stimulus, such as a pH variation or the action of an enzyme. In another particular embodiment, the carrier allows the release of the compound(s) of interest in response to an external stimulus. Examples of external stimulus are electromagnetic radiations (for example an ionizing radiation such as X-ray, gamma-ray or a non-ionizing radiation such as UV, visible light or infra-red), ultrasounds and a magnetic field. The pharmaceutical compound is for example released from the carrier when said carrier is exposed to an external stimulus selected from electromagnetic radiations, ultrasounds and a magnetic field.

A carrier devoid of any surface sterically stabilizing agent can be for instance a liposome with a membrane phase transition temperature comprised between 37° C. and 45° C. comprising DiPalmitoylPhosphatidylCholine (DPPC) 62% mol, Hydrogenated Soybean PhophatidylCholine (HSPC) 22% mol and Cholesterol (Chol) 16% mol, or DiPalmitoyl-PhosphatidylCholine (DPPC) 90% mol and MonoPalmitoyl-Phosphatidylcholine (MPPC) 10% mol.

A carrier devoid of any surface sterically stabilizing agent can also be for instance a liposome comprising a synthetic phospholipid, such as 1,3-diamidophospholipid sensitive to shear stress.

A carrier devoid of any surface sterically stabilizing agent can also be for instance a liposome comprising a peptide, which changes its conformation (alpha-helix to beta-sheet) upon pH or temperature stimuli.

A carrier devoid of any surface sterically stabilizing agent can also be for instance an amphoteric liposome comprising 1-palmitoyl-2oleoyl-sn-glycero-3-phosphocholine (POPC) and 1,2-dioleoyl-sn-glycero-3-phosphoethanolamine (DOPE) in a molar ratio 3:1 and an equal amount of a weak cationic and a weak anionic amphiphiles, both derived from cholesterol, α-(3'-O-cholesteryloxycarbonyl)-6-(N-ethylmorpholine)-succinamide (MoChol) and cholesteryl-hemisuccinate (CHEMS).

The pharmaceutical composition of the invention (defined by the combination of the at least one biocompatible nanoparticle and of the at least one carrier comprising at least one compound of interest) can be used in many fields, in particular in human or veterinary medicine. This composition is typically for use in an animal, preferably in a mammal, even more preferably in a human being, whatever its age or sex.

The pharmaceutical composition of the invention can be used to prevent or treat a disease or disorder selected from a cardiovascular disease, a Central Nervous System (CNS) disease, a gastrointestinal disease, a genetic disorder, a hematological disorder, a hormonal disorder, an immune disorder, an infectious disease, a metabolic disorder, a musculoskeletal disorder, a cancer, a respiratory disease and an intoxication, etc. In a preferred embodiment, the pharmaceutical composition is for use for preventing or treating a disease or disorder selected from a cardiovascular disease, a CNS disease, a cancer, an infectious disease and a metabolic disorder.

In the context of the present invention, the at least one nanoparticle and the at least one carrier comprising the compound(s) of interest are advantageously to be administered in a subject in need of said compound(s) of interest, between more than 5 minutes and about 72 hours one from each other, typically between more than 5 minutes and about 24 hours, preferably between more than 5 minutes or 30 minutes and about 12 hours, in order to optimize the compound(s) pharmaceutical efficacy.

In the present invention, when the at least one nanoparticle and the at least one carrier comprising the compound(s) of interest are advantageously to be administered in a subject in need of said compound, between more than 5 minutes and about 72 hours one from each other, the absolute surface charge value of the at least one biocompatible nanoparticle is of at least 10 mV (|10 mV|).

In a particular embodiment of the present invention, when the at least one nanoparticle and the at least one carrier comprising the compound(s) of interest are advantageously to be administered in a subject in need of said compound, between more than 5 minutes and about 24 hours one from each other, the absolute surface charge value of the at least one biocompatible nanoparticle is advantageously of at least 15 mV (|15 mV|).

In another particular embodiment of the present invention, when the at least one nanoparticle and the at least one carrier comprising the compound(s) of interest are advantageously to be administered in a subject in need of said compound, between more than 5 minutes and about 12 hours one from each other, the absolute surface charge value of the at least one biocompatible nanoparticle is advantageously of at least 20 mV (|20 mV|).

Also herein described is a method of preventing or treating a subject suspected to be predisposed to a disease, or suffering of a disease, such as those herein mentioned, wherein said method comprises administering to said subject a pharmaceutical composition of the invention, typically at least one biocompatible nanoparticle and at least one carrier comprising at least one compound of interest as herein described. Anyone of the at least one nanoparticle or at least one carrier comprising the compound(s) of interest can be administered first to the subject as long as the at least one biocompatible nanoparticle and the at least one carrier comprising the compound(s) are administered separately, typically in an interval of between more than 5 minutes and about 72 hours. Administration of said at least one nanoparticle or at least one carrier comprising compound(s) of interest can be a single administration of each, repeated administrations of each, for example several consecutive administrations of each. The biocompatible nanoparticle may be administered once and the at least one carrier comprising compound(s) of interest may be administered more than once and vice versa.

In a particular embodiment, the at least one biocompatible nanoparticle is at least administered at the beginning of a protocol comprising several administrations of the at least one carrier comprising compound(s) interest, i.e. at least at the first administration of said at least one carrier and before or after the administration thereof.

In another particular embodiment, the biocompatible nanoparticle is not administered at the beginning of a protocol comprising several administrations of the at least one carrier comprising a compound(s) of interest and is not administered before the second or third administration of said at least one carrier, and before or after the administration thereof.

In the context of these last two embodiments, the at least one biocompatible nanoparticle can also be administered together (before or after as previously explained) with the at least one carrier comprising the compound(s) of interest during part or all of the subsequent administrations of said at least one carrier.

The biocompatible nanoparticle(s) of the pharmaceutical composition of the invention can be administered by any route such as intra venous (IV), intra-arterial, intra peritoneal route, intra-dermic route, airways (inhalation), intra muscular route and/or oral route (per os). A preferred route of administration is the intra venous route.

The carrier(s) comprising the compound(s) of interest of the pharmaceutical composition of the invention can be administered by any route selected from subcutaneous route, intra venous (IV) route, intra-dermic route, intra-arterial route, airways (inhalation), intra peritoneal route, intra muscular route, oral route (per os) and several distinct routes among those previously mentioned. The adequate route(s) will be selected by the practitioner depending on the disease or disorder to be detected, prevented or treated.

The following examples illustrate the invention without limiting its scope.

EXAMPLES

Example 1: Synthesis no 1 of Liposomes as Biocompatible Nanoparticles

Liposomes are prepared using the lipidic film re-hydration method:
a) Lipids are solubilized in chloroform. Chloroform is finally evaporated under a nitrogen flow. Re-hydration of the lipidic film with HEPES 20 mM and NaCl 140 mM at pH 7.4 is performed at 50° C., so that the lipidic concentration is 5 mM.

The following lipidic composition was used to prepare charged liposomes: DPPC (DiPalmitoylPhosphatidylCholine): 86% mol; MPPC (MonoPalmitoylPhosphatidylcholine): 10% mol; DSPE-PEG (DiStearylPhosphatidylEthanolamine-[methoxy(PolyElthyleneGlycol)-2000]): 4% mol.
b) Freeze-thaws cycles are then performed 6 times, by successively plunging the sample into liquid nitrogen and into a water bath regulated at 50° C.
c) A thermobarrel extruder (LIPEX™ Extruder, Northern Lipids) was used to calibrate the size of the liposomes under controlled temperature and pressure. In all cases, extrusion was performed at 50° C., under a pressure of 10 bars.

Size distribution of the as-prepared liposomes was determined by dynamic light scattering (DLS) using a Zetasizer NanoZS (Malvern instrument) with a 633 nm HeNe laser at an angle of 90° C. The liposomes suspension was diluted 100 times in HEPES 20 mM and NaCl 140 mM at pH 7.4. Liposome size (i.e. hydrodynamic diameter) was equal to about 170 nm (distribution by intensity) with a polydispersity index (PDI) equal to about 0.1.

As understandable by the skilled person, the desired surface charge was obtained thanks to the selected lipidic composition, and its value is confirmed by zeta potential measurement using a Zetasizer NanoZS (Malvern instrument).

The liposomes were diluted 100 times in water and the pH of the resulting suspension was adjusted to pH 7.4. The liposome surface charge was equal to about −14 mV at pH 7.4.

Example 2: Synthesis n° 2 of Liposomes as Biocompatible Nanoparticles

Liposomes are prepared using the lipid film re-hydration method:
a) Lipids are solubilized in chloroform. Chloroform is finally evaporated under a nitrogen flow. Re-hydration of the lipid film with HEPES 20 mM and NaCl 140 mM at pH 7.4 is performed at 65° C., so that the lipid concentration is 25 mM.

The following lipid composition was used to prepare liposomes: DSPC (DiStearoylPhosphatidylCholine): DSPG (DiStearoylPhosphatidylGlycerol): CHOL (Cholesterol) in a 7:2:1 molar ratio.
b) Freeze-thaw cycles are then performed 6 times, by successively plunging the sample into liquid nitrogen and into a water bath regulated at 65° C.
c) A thermobarrel extruder (LIPEX™ Extruder, Northern Lipids) was used to calibrate the size of the liposomes under controlled temperature and pressure. First, 5 passages were performed through a polyethersulfone (PES) 0.45 μm-pores sized membrane at 5 bars, then 10 passages through a PES 0.22 μm-pores sized membrane at 10 bars, and finally 10 passages through a polyvinylidene fluoride (PVDF) 0.1 μm-pores sized membrane at 15 bars.

Size distribution of the as-prepared liposomes was determined by dynamic light scattering (DLS) using a Zetasizer NanoZS (Malvern instrument) with a 633 nm HeNe laser at an angle of 90° C. The liposomes suspension was diluted 100 times in HEPES 20 mM and NaCl 140 mM at pH 7.4. Liposome size (i.e. hydrodynamic diameter) was equal to about 145 nm (distribution by intensity) with a polydispersity index (PDI) equal to about 0.1. The desired surface charge, which is typically below −10 mV, was obtained thanks to the selected lipidic composition, and its value is confirmed by zeta potential measurement using a Zetasizer NanoZS (Malvern instrument).

Example 3: Method Allowing an Improved Efficacy and/or a Reduced Toxicity Following the Administration to a Subject of a Compound of Interest Included in the Pharmaceutical Composition According to the Invention when Compared to the Same Dose of the Compound of Interest Alone A pharmaceutical composition according to claim 1 comprising the combination of (i) at least one biocompatible nanoparticle and of (ii) at least one carrier comprising doxorubicin, is administered in nude mice bearing a MDA-MB-231-lucD3H2LN xenografted tumor in the following manner:
a) administering to a first group of nude mice (by intra venous injection) the Dox-NP® (a PEGylated liposomal formulation of doxorubicine);
administering to a second group of nude mice (by intra venous injection) the doxorubicine;
administering to a third group of nude mice (by intra venous injection) the biocompatible nanoparticles;
administering to a fourth group of nude mice (by intra venous injection) the biocompatible nanoparticles and, between more than 5 minutes and 72 hours following the administration of the biocompatible nanoparticles to the fourth group of nude mice, administering (by intra venous injection) to said fourth group of nude mice a carrier comprising the doxorubicin wherein the carrier is devoid of any sterically stabilizing agent;
b) assessing any clinical sign of toxicity in nude mice after the administration of the Dox-NP® (first group), the doxorubicin (second group), the biocompatible nanoparticles (third group) and the pharmaceutical composition (fourth group); and
c) measuring the tumor re-growth delay after the administration of the Dox-NP® (first group), the doxorubicin (second group) the biocompatible nanoparticles (third group) and the pharmaceutical composition (fourth group).

Example 4: Synthesis n° 3 of Liposomes as Biocompatible Nanoparticles

Liposomes are prepared using the lipid film re-hydration method:
a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C., so that the lipid concentration is 50 mM.

The following lipid composition was used to prepare charged liposomes: DPPC (DiPalmitoylPhosphatidylCholine) 58% mol; HSPC (Hydrogenated Soybean PhosphatidylCholine) 21% mol; CHOL (Cholesterol) 16% mol; POPS (1-Palmitoyl-2-Oleoyl PhosphatidylSerine) 5% mol.
b) Freeze-thaw cycles are then performed 6 times, by successively plunging the sample into liquid nitrogen and into a water bath regulated at 60° C. Ultra-sonication of the liposomes solution is performed during 30 s every 3 freeze-thaw cycles and just before extrusion.
c) A thermobarrel extruder (LIPEX™ Extruder, Northern Lipids) is used to calibrate the size of the liposomes under controlled temperature and pressure. Extrusion is performed at 60° C. Ten passages are applied through a 0.11 μm pores size polyvinylidene fluoride (PVDF) membrane under a pressure of 10 bars.

Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is equal to about 170 nm (distribution by intensity) with a polydispersity index (PdI) equal to about 0.2.

As understandable by the skilled person, the desired surface charge is obtained thanks to the selected lipid composition, and its value is confirmed by zeta potential measurement using a Zetasizer NanoZS (Malvern instrument). The liposomes are diluted 200 times in a sodium chloride solution at 1 mM and the pH of the solution is adjusted to pH 7. The liposomes surface charge is equal to about −40 mV at pH 7, NaCl 1 mM.

The final lipid concentration of the liposomes solution is measured by a colorimetric assay (Bartlett method). The method is based on total phosphorus determination through an acidic digestion of phospholipid. The released inorganic phosphate is reacted with ammonium molybdate, the complex giving a strong blue color. Lipids concentration is equal to about 50 mM.

Example 5: Synthesis n° 4 of Liposomes as Biocompatible Nanoparticles

Liposomes are prepared using the lipid film re-hydration method:
a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C., so that the lipid concentration is 50 mM.
The following lipid composition was used to prepare the charged liposomes: DPPC (DiPalmitoylPhosphatidylCholine) 45.15% mol; CHOL (Cholesterol) 45.15% mol; DSPE-PEG (DiStearylPhosphatidylEthanolamine-[methoxy(Poly-ElthyleneGlycol)-2000]) 0.60% mol; L-Glutamic acid, N-(3-carboxy-1-oxopropyl)-, 1,5-dihexadecyl ester (SA-lipid) 9.10% mol. The SA-lipid brings COOH groups on the liposomes surface.
b) Freeze-thaw cycles are then performed 6 times, by successively plunging the sample into liquid nitrogen and into a water bath regulated at 60° C.
c) A thermobarrel extruder (LIPEX™ Extruder, Northern Lipids) is used to calibrate the size of the liposomes under controlled temperature and pressure. Extrusion is performed at 60° C. Seven passages are applied through a 0.451 μm pores size polyvinylidene fluoride (PVDF) membrane under a pressure of 3 bars and ten passages through a 0.221 μm pores size polyvinylidene fluoride (PVDF) membrane under a pressure of 10 bars. Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is equal to about 230 nm (distribution by intensity) with a polydispersity index (PdI) equal to about 0.2.

As understandable by the skilled person, the desired surface charge is obtained thanks to the selected lipid composition, and its value is confirmed by zeta potential measurement using a Zetasizer NanoZS (Malvern instrument). The liposomes solution is diluted 200 times in a sodium chloride solution at 1 mM and the pH of the solution is adjusted to pH 7.

The liposomes surface charge is equal to about −60 mV at pH 7, NaCl 1 mM. The final lipid concentration of the liposomes solution is measured by a colorimetric assay (Bartlett method). The method is based on total phosphorus determination through an acidic digestion of phospholipid. The released inorganic phosphate is reacted with ammonium molybdate and the complex giving a strong blue color. Lipids concentration is equal to about 50 mM.

Example 6: Synthesis n° 5 of Liposomes as Biocompatible Nanoparticles

Liposomes are prepared using the lipid film re-hydration method:
a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C. and the lipid concentration is 50 mM.
The following lipid composition was used to prepare the charge liposomes: DSPC (1,2-distearoyl-sn-glycero-3-phosphocholine) 60% mol, CHOL (Cholesterol) 35% mol; and Succinyl PE (1,2-dioleoyl-sn-glycero-3-phosphoethanolamine-N-succinyl) 5% mol.
b) Freeze-thaw cycles are then performed 6 times, by successively plunging the sample into liquid nitrogen and into a water bath regulated at 60° C. Ultra-sonication of the liposomes solution is performed during 30 s, every 3 freeze-thaw cycles and just before extrusion.
c) A thermobarrel extruder (LIPEX™ Extruder, Northern Lipids) is used to calibrate the size of the liposomes under controlled temperature and pressure. Extrusion is performed at 60° C. Twelve passages are applied through a 0.22 μm pores size polyvinylidene fluoride (PVDF) membrane under a pressure of 12 bars.
d) Conjugation of p-aminophenyl-α-D-mannopyranoside (MAN) to Succinyl PE liposome:
The succinyl PE liposome surface are modified with a mannose derived ligand p-aminophenyl-α-D-mannopyranoside (MAN), using carbodiimide coupling to develop mannose conjugated liposome. MAN is covalently coupled by its amino group to the carboxylic acid group of Succinyl PE, present on the surface of preformed Succinyl PE liposome. Briefly, to the preformed Succinyl PE liposome solution are added EDC (1-ethyl-3-[3-dimethylaminopropyl] carbodiimide hydrochloride), (Succinyl PE/EDC 1:10 molar ratio) and N-hydroxysuccinimide (NHS) (NHS/EDC 1:2.5 molar ratio). The pH of the suspension is then adjusted at 6 with NaOH 1M and the resulting suspension is stirred for 15 minutes at room temperature. Subsequently, the pH of the solution is adjusted at 7 with NaOH 1M and the aqueous MAN solution is added (Succinyl PE/MAN 1:2 molar ratio) to the solution. pH is readjusted at 7 using NaOH 1M and the suspension is stirred for 2 additional hours at room temperature. Excessive unbound MAN, EDC and NHS molecules are removed by 3 steps of dialysis with dilution factor (×500; ×500; ×500) using a 50 KDa cellulose membrane.

Of note, due to possible dilution upon dialysis, the liposomes solution can be concentrated by centrifugation (typically a Sigma 3-15K centrifuge at 5° C.; 1,200 rpm) using membrane ultrafiltration on Vivaspin concentrators with a polyethylene sulfone (PES) membrane and a cut-off 300 KDa.

Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is about 230 nm (distribution by intensity) with a polydispersity index (PDI) around 0.2. As understandable by the skilled person, the desired surface charge is obtained thanks to the selected lipid composition, and its value is confirmed by zeta potential measurement using a Zetasizer NanoZS (Malvern instrument). The liposomes solution is diluted 200 times in a sodium chloride solution at 1 mM and at pH 7. The liposomes surface charge is around −70 mV at NaCl 1 mM, pH 7. The final lipid concentration of the liposomes solution is measured by a colorimetric assay (Bartlett method). The method is based on total phosphorus determination through an acidic digestion of phospholipid. The released inorganic phosphate is reacted with ammonium molybdate and the complex giving a strong blue color. Lipids concentration is equal to about 50 mM.

The invention claimed is:

1. A method for treating cancer in a subject, the method comprising a step of intravenously administering to the subject at least one carrier comprising at least one pharmaceutical compound, the at least one pharmaceutical compound being encapsulated in the at least one carrier, and the at least one pharmaceutical compound being a chemotherapeutic agent, and a distinct step of intravenously administering to the subject at least one biocompatible lipid-based nanoparticle, wherein the at least one carrier is devoid of any surface sterically stabilizing agent and wherein the longest dimension of the at least one biocompatible nanoparticle is between about 4 nm and about 500 nm, the surface charge value of the at least one biocompatible nanoparticle is a negative surface charge value below −10 mV, the at least one biocompatible nanoparticle is not used as a pharmaceutical compound, and said at least one biocompatible nanoparticle is administered to the subject about 10 minutes, or more than 10 minutes, and less than about 72 hours before administering the at least one carrier comprising the at least one pharmaceutical compound.

2. The method according to claim 1, wherein the nanoparticle is further covered with a biocompatible coating.

3. The method according to claim 1, wherein the carrier is a plain carrier.

4. The method according to claim 1, wherein the carrier is a hollow carrier.

5. The method according to claim 1, wherein the carrier's surface is devoid of any hydrophilic polymer.

6. The method according to claim 1, wherein the carrier's surface is devoid of polyethylene glycol (PEG) polymer.

7. The method according to claim 1, wherein the administration of the at least one biocompatible nanoparticle and of the at least one carrier comprising the pharmaceutical compound(s) maintains the therapeutic benefit of said pharmaceutical compound(s) and reduces toxicity, or increases the therapeutic benefit of said pharmaceutical compound(s) for an equivalent or reduced toxicity, for the subject, when compared to therapeutic benefit and toxicity induced by the standard therapeutic dose(s) of said compound(s) in the absence of any biocompatible nanoparticle and/or carrier.

8. The method according to claim 1, wherein the administration of the at least one biocompatible nanoparticle and of the at least one carrier comprising the pharmaceutical compound(s) allows a reduction of at least 10% of the administered pharmaceutical compound(s) therapeutic dose(s) when compared to the standard therapeutic dose(s) of said compound(s) while maintaining the same therapeutic benefit for an equivalent toxicity or a reduced toxicity for the subject or while increasing the therapeutic benefit for an equivalent or reduced toxicity for the subject in the absence of any biocompatible nanoparticle and/or carrier.

9. The method according to claim 1, wherein the nanoparticle is cleared from the subject to whom it has been administered within one hour and six weeks after its administration to a subject in need of said at least one pharmaceutical compound.

10. The method according to claim 1, wherein the chemotherapeutic agent is selected from a small molecule, a targeted small molecule, a cytotoxic compound and a transition metal coordination complex.

11. The method according to claim 1, wherein the pharmaceutical compound is released from the carrier by temporal-controlled diffusion, carrier erosion and/or carrier degradation.

12. The method according to claim 1, wherein the pharmaceutical compound is released from the carrier in response to an intracellular or an extracellular stimulus.

13. The method according to claim 1, wherein the pharmaceutical compound is released from the carrier when said carrier is exposed to electromagnetic radiation, ultrasound or a magnetic field.

14. The method according to claim 1, wherein said at least one biocompatible nanoparticle is administered to the subject about 10 minutes before administering the at least one carrier comprising at least one pharmaceutical compound.

15. The method according to claim 1, wherein said at least one biocompatible nanoparticle is administered to the subject more than 10 minutes and less than about 24 hours before administering the at least one carrier comprising at least one pharmaceutical compound.

16. The method according to claim 1, wherein said carrier is devoid of a surface sterically stabilizing agent selected from Dextran, polysialic acid (PSA), hyaluronic acid, chitosan, heparin, polyvinyl pyrrolidone (PVP), polyvinyl alcohol (PVA), polyacrylamide, poly(ethylene glycol) (PEG), poloxamer, poloxamine or polysorbate.

* * * * *

UNITED STATES PATENT AND TRADEMARK OFFICE
CERTIFICATE OF CORRECTION

PATENT NO. : 10,765,632 B2
APPLICATION NO. : 15/529106
DATED : September 8, 2020
INVENTOR(S) : Matthieu Germain et al.

Page 1 of 1

It is certified that error appears in the above-identified patent and that said Letters Patent is hereby corrected as shown below:

In the Specification

Column 10,
Lines 45-46, "α-(3'-O-cholesteryloxycarbonyl)-6-(N-ethylmorpholine)-succinamide" should read --α-(3'-O-cholesteryloxycarbonyl)-δ-(N-ethylmorpholine)-succinamide--.

Column 14,
Lines 55-56, "0.11μm" should read --0.1μm--.

Column 15,
Line 43, "0.451 μm" should read --0.45μm--.
Line 45, "0.221 μm" should read --0.22μm--.

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*